(12) United States Patent
Nagaoki et al.

(10) Patent No.: US 6,472,663 B2
(45) Date of Patent: Oct. 29, 2002

(54) ELECTRON MICROSCOPE

(75) Inventors: Isao Nagaoki, Hitachinaka (JP); Hiroyuki Kobayashi, Mito (JP); Takafumi Yotsuji, Hitachinaka (JP)

(73) Assignees: Hitachi, Ltd., Tokyo (JP); Hitachi Instruments Engineering Co., Ltd., Hitachinaka (JP)

( * ) Notice: Subject to any disclaimer, the term of this patent is extended or adjusted under 35 U.S.C. 154(b) by 0 days.

(21) Appl. No.: 09/182,356

(22) Filed: Oct. 29, 1998

(65) Prior Publication Data

US 2002/0033451 A1 Mar. 21, 2002

(30) Foreign Application Priority Data

Oct. 30, 1997 (JP) .............................................. 9-298410

(51) Int. Cl.$^7$ ................................................ H01J 31/26
(52) U.S. Cl. ....................................... 250/311; 250/310
(58) Field of Search ............................ 250/311, 396 R, 250/396 ML, 310, 307

(56) References Cited

U.S. PATENT DOCUMENTS

| | | | | |
|---|---|---|---|---|
| 4,091,374 A | * | 5/1978 | Muller et al. ................. 250/311 |
| 4,724,319 A | * | 2/1988 | Shirota ........................ 250/311 |
| 4,866,273 A | * | 9/1989 | Kobayashi et al. ......... 250/311 |
| 5,013,913 A | * | 5/1991 | Benner ........................ 250/311 |
| 5,519,216 A | * | 5/1996 | Benner et al. .............. 250/311 |
| 5,777,327 A | * | 7/1998 | Mizuno ........................ 250/310 |

FOREIGN PATENT DOCUMENTS

JP 61-071539 12/1986

* cited by examiner

*Primary Examiner*—Jack Berman
(74) *Attorney, Agent, or Firm*—Kenyon & Kenyon

(57) ABSTRACT

Relationship among an exciting current of each lens of an irradiation lens system including at least two stages of irradiation lenses and an electron beam aperture, an irradiation electron beam density on a sample and an area of the sample surface irradiated with an electron beam is stored in a form of a table or equations, and an exciting condition of each of the lenses of the irradiation lens system is retrieved from the relationship and set the irradiation lens system to the retrieved condition, for example, when the enlarging magnification is changed under a condition of keeping the irradiation electron beam density at a constant value. Further, trails of a region of the sample surface irradiated with the electron beam is displayed on a display unit.

4 Claims, 8 Drawing Sheets

ELECTRON MICROSCOPE

BACKGROUND OF THE INVENTION

The present invention relates to an electron microscope and particularly to a method of controlling an electron optical condition of an irradiation lens system in a transmission electron microscope to reduce damage of a sample by an irradiation electron beam and a display apparatus therefor.

The transmission electron microscope is an apparatus by which an inner structure of a sample can be observed by focusing electrons passing though the sample or a lattice image can be observed using a diffraction wave. In recent years, the transmission electron microscope is used for structural analysis of biological materials such as protein, DNA, RNA and the like.

Up to now, in order to obtain a brightness of an enlarged image of a sample suitable for observation or picture-taking when the enlarged image is observed using a transmission electron microscope of a general two-stage irradiation lens type, the appropriate brightness has been set by changing a lens current of a second irradiation lens which is placed near the sample. Otherwise, adjustment of the brightness of the enlarged image has been performed by changing a bias voltage of a high voltage control unit to increase or decrease an electron beam current.

In the former method, when the brightness of the enlarged image is changed, an irradiated region (area) on the sample surface irradiated with the electron beam irradiating is changed and a portion (region) on the sample other than the region necessary for the observation or the picture-taking is irradiated with unnecessary electrons. Accordingly, the region of the sample surface unnecessary for the observation or the picture-taking may be also damaged. The electron beam irradiation damages the portion on the sample surface other than the region which has once been observed or formed into a picture, which may cause the next observation or picture-taking cannot be performed. That is, the efficiency of microscopic examination is extremely deteriorated by narrowing the region to be observed or to be formed into a picture, or by frequent exchange of the sample in some cases.

In the latter method, although the electron irradiated region on the sample surface is varied not so much, there has been a limitation in increasing the brightness of the enlarged image because the beam current cannot output above several tens $\mu A$ due to capacity of the high voltage circuit. Further, when the bias voltage is excessively lowered, an unsaturated image of the filament appears to occur unevenness in the brightness of the enlarged image though the beam current can be increased. Therefore, the changing of the brightness by changing the beam current is not practical due to the narrow variable range.

SUMMARY OF THE INVENTION

An object of the present invention is to provide a transmission electron microscope which can solve the above-mentioned problem, and can irradate only a region of a sample necessary for observation or taking picture of the image with the electron beam with a necessary beam current to reduce the sample damage by unnecessary electron irradiation.

The above object of the present invention can be attained by providing an electron microscope with a function that relationship among an exciting current of each lens of an irradiation lens system including at least two stages of irradiation lenses and an electron beam aperture, an irradiation electron beam density onto a sample and an area of the sample surface irradiated with an electron beam is stored in a form of a table or an equation, and an exciting condition of each of the lenses of the irradiation lens system is retrieved from the relationship and set the irradiation lens system to the retrieved condition, for example, when the enlarging magnification is changed under a condition of keeping the irradiation electron beam density at a constant value or when the enlarging magnification is changed under a condition of keeping the brightness of a sample image at a constant value. Further, the above object of the present invention can be attained by that a region on a sample surface to be observed, for example, a region completely without sample damage with the electron beam can be efficiently selected by displaying trails of a region of the sample surface irradiated by the electron beam on a display unit.

That is, the present invention is characterized by an electron microscope comprising an electron beam source; at least two stages of irradiation lenses; an aperture capable of shading part of an electron beam emitted from the electron beam source; and a lens control means for controlling the irradiation lenses, a sample being irradiated with the electron beam focused by the irradiation lens and limited by the aperture, wherein the irradiation lens control means comprises a function to change a density of the irradiation electron beam while an area of an electron beam irradiation region on a sample surface is being kept to a nearly constant value.

Further, the present invention is characterized by an electron microscope comprising an electron beam source; at least two stages of irradiation lenses; an aperture capable of shading part of an electron beam emitted from the electron beam source; and a lens control means for controlling the irradiation lenses, a sample being irradiated with the electron beam focused by the irradiation lens and limited by the aperture, wherein the irradiation lens control means comprises a function to switch an area of an electron beam irradiation region on a sample surface in interlocking with an enlarging magnification of the electron microscope every time when the magnification is changed; and a function to change a density of the irradiation electron beam while the area of the electron beam irradiation region on the sample surface is being kept to a nearly constant value.

It is preferable that the irradiation lens control means comprises a function to convert an image acquisition region of an enlarged image, that is, a region of an enlarged image to be observed, recorded and displayed (typically, a region of an image capable of being acquired by a TV camera attached to the microscope) into a region on the sample surface using an enlarging magnification and to control so that the converted region becomes an electron beam irradiation region.

Further, the present invention is characterized by an electron microscope comprising an electron beam source; at least two stages of irradiation lenses; an aperture capable of shading part of an electron beam emitted from the electron beam source; and a lens control means for controlling the irradiation lenses, a sample being irradiated with the electron beam focused by the irradiation lens and limited by the aperture, wherein the irradiation lens control means comprises a function to change an area of an electron beam irradiation region while a density of the electron beam irradiating on a sample surface is being kept at a nearly constant value.

It is preferable that the irradiation lens control means comprises a function to switch said value of irradiation electron beam density kept at a nearly constant value in interlocking with an enlarging magnification of said electron microscope every time when the magnification is changed.

An electron microscope in accordance with the present invention comprises an input means for setting the irradiation electron beam density or for setting the area of the electron beam irradiating region.

Further, the present invention is characterized by an electron microscope comprising irradiation lenses and a sample fine movement apparatus, a sample surface being irradiated with an electron beam focused by said irradiation lenses, which further comprises a function for displaying a region of a sample surface irradiated with the electron beam based on information on the region irradiated by the electron beam and sample position information from the sample fine movement apparatus.

Furthermore, the present invention is characterized by an electron microscope comprising irradiation lenses and a sample fine movement apparatus, a sample surface being irradiated with an electron beam focused by said irradiation lenses, which further comprises a function for displaying a region of a sample surface irradiated by the electron beam with varying a display condition, for example, brightness (halftones) or display color corresponding to a quantity of irradiated electron beam based on a region irradiated with the electron beam, an irradiation electron beam density, an irradiation time period and sample position information from the sample fine movement apparatus.

An electron microscope in accordance with the present invention comprises a means for taking a picture of an enlarged image of the electron microscope and a means for displaying the picture of the image, and the display of the region of the sample surface irradiated with the electron beam may be displayed by overlapping onto the picture of the enlarged sample image.

DESCRIPTION OF THE PREFERRED EMBODIMENTS

Figure 1:
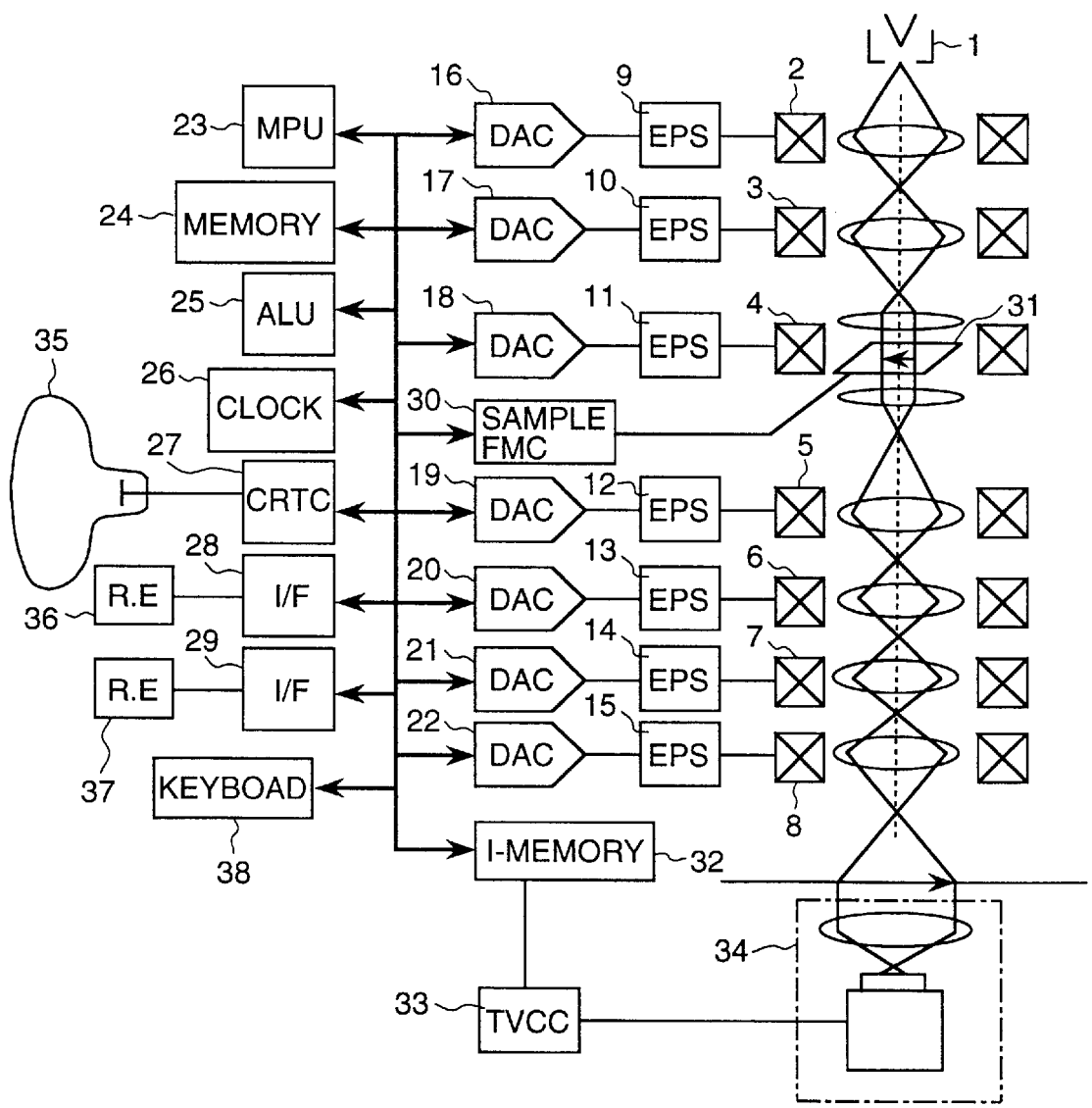
FIG. 1 is a schematic diagram showing the construction of a transmission electron microscope in accordance with the present invention.

Operation of an electron microscope in accordance with the present invention will be described below. Initially, a control unit reads information on changing an irradiation electron beam density from a means for inputting a brightness of an enlarged image, that is, an irradiation electron beam density. Then, the control unit retrieves an appropriate combination of a first irradiation lens current and a second irradiation lens current based on an irradiation electron beam density to be set derived from the information on changing from the present irradiation electron beam density using a calculation function out of pre-stored data of combinations of a first irradiation lens current and a second irradiation lens current keeping an electron beam irradiation region constant from the present electron beam irradiation region. When any combination of a first irradiation lens current and a second irradiation lens current for the irradiation electron beam density to be set does not exist, a first irradiation lens current and a second irradiation lens current to be set are derived through an interpolation calculation using combinations of data near the irradiation electron beam density.

Otherwise, current values of a first irradiation lens 39 and a second irradiation lens 40 are calculated through calculation using input data of an irradiation electron beam density and an area of electron beam irradiation region. An outline of this calculation method will be explained below, referring to an example of an irradiation lens system shown in FIG. 10.

Let a quantity of an electron beam generated from an electron gun 1 be $I_1$, a radius of a first irradiation lens fixed aperture 51 be $R_1$, a radius of an irradiation lens aperture 47 be $R_2$, a radius of the electron beam on the surface of the irradiation lens aperture 47 be R, a radius of an electron beam irradiation region on a sample surface be $R_3$, and a focal length of a first irradiation lens 39 be f. In the irradiation lens system shown in FIG. 10, the irradiation electron beam density is controlled by adjusting the quantity of electron beam to be shaded by the irradiation lens aperture 47. Values of the dimensions $A_1$, $R_1$, $R_2$, $L_1$ and $L_2$ are constants determined from the construction of the electron microscope. Further, there are relationships $R > R_2$, $L_1 > B_1$ from a method of using the irradiation lens system.

Let the irradiation area on the surface of a sample 42 be S, the following equation 1 is satisfied.

$$S = \pi R_3^2 \tag{1}$$

When a quantity of the electron beam on the sample surface is let be $I_2$, an irradiation electron beam density j on the sample surface is expressed by the following equation 2.

$$j = \frac{I_2}{S} = \frac{I_2}{\pi R_3} \tag{2}$$

The quantity of the electron beam on the sample surface $I_2$ can be expressed by the following equation 3 from the equation 2.

$$I_2 = j\pi R_3^2 \tag{3}$$

Further, the quantity of the electron beam on the sample surface $I_2$ can be expressed by the following equation 4 using the quantity of electron beam $I_1$ at a cross-over 48 and the radius $R_2$ of the irradiation lens aperture 47 and the radius R of the electron beam on the surface of the irradiation lens aperture 47.

$$I_2 = I_1 \left[\frac{R_2}{R}\right]^2 \quad (4)$$

By transforming the equation 4, the following equation 5 can be obtained.

$$R = R_2 \sqrt{\frac{I_1}{I_2}} \quad (5)$$

By substituting the equation 5 into the equation 3, the following Equation 6 can be obtained.

$$R = R_2 \sqrt{\frac{I_1}{j\pi R_3^2}} \quad (6)$$

Next, the relationship between R and the current value of the first irradiation lens 39 is calculated. The focal length f of the first irradiation lens 39 can be expressed by the following approximation equation 7, where the lens current is i and C is a constant.

$$f = \frac{C}{i^2} \quad (7)$$

The relation of the following equation 8 is satisfied by an electronic optical equation.

$$\frac{1}{A_1} + \frac{1}{B_1} = \frac{1}{f} \quad (8)$$

Therein, when $A_1 \gg B_1$, the following equation 9 is satisfied.

$$B \ll f \quad (9)$$

From FIG. 19, the following equation 10 can be derived.

$$\frac{R_1}{f} = \frac{R}{L_1 - f} \quad (10)$$

From the equation 10, the focal length f of the first irradiation lens 39 can be expressed by the following equation 11.

$$f = L_1 \frac{R_1}{R + R_1} \quad (11)$$

By substituting the equation 7 into the equation 11, the lens current value i of the first irradiation lens 39 becomes the following equation 12.

$$i^2 = C \frac{R + R_1}{L_1 \times R_1} \quad (12)$$

By substituting the equation 6 into the equation 12, the following equation 13 can be obtained.

$$i^2 = C \frac{R_2 \sqrt{\frac{I_1}{j\pi R_3^2}} + R_1}{L_1 \times R_1} \quad (13)$$

From the equation 13, the lens current value i of the first irradiation lens 39 can be calculated by inputting the irradiation electron beam density j on the sample surface and the radius $R_3$ of the electron irradiation region.

Next, the lens current value i' of the second irradiation lens 40 is calculated. Using the equation 8 of the electron optical equation, the relation among A, B and the focal length f' of the second irradiation lens 40 can be expressed by the following equation 14.

$$\frac{1}{A_2} + \frac{1}{B_2} = \frac{1}{f'} \quad (14)$$

Figure 10:
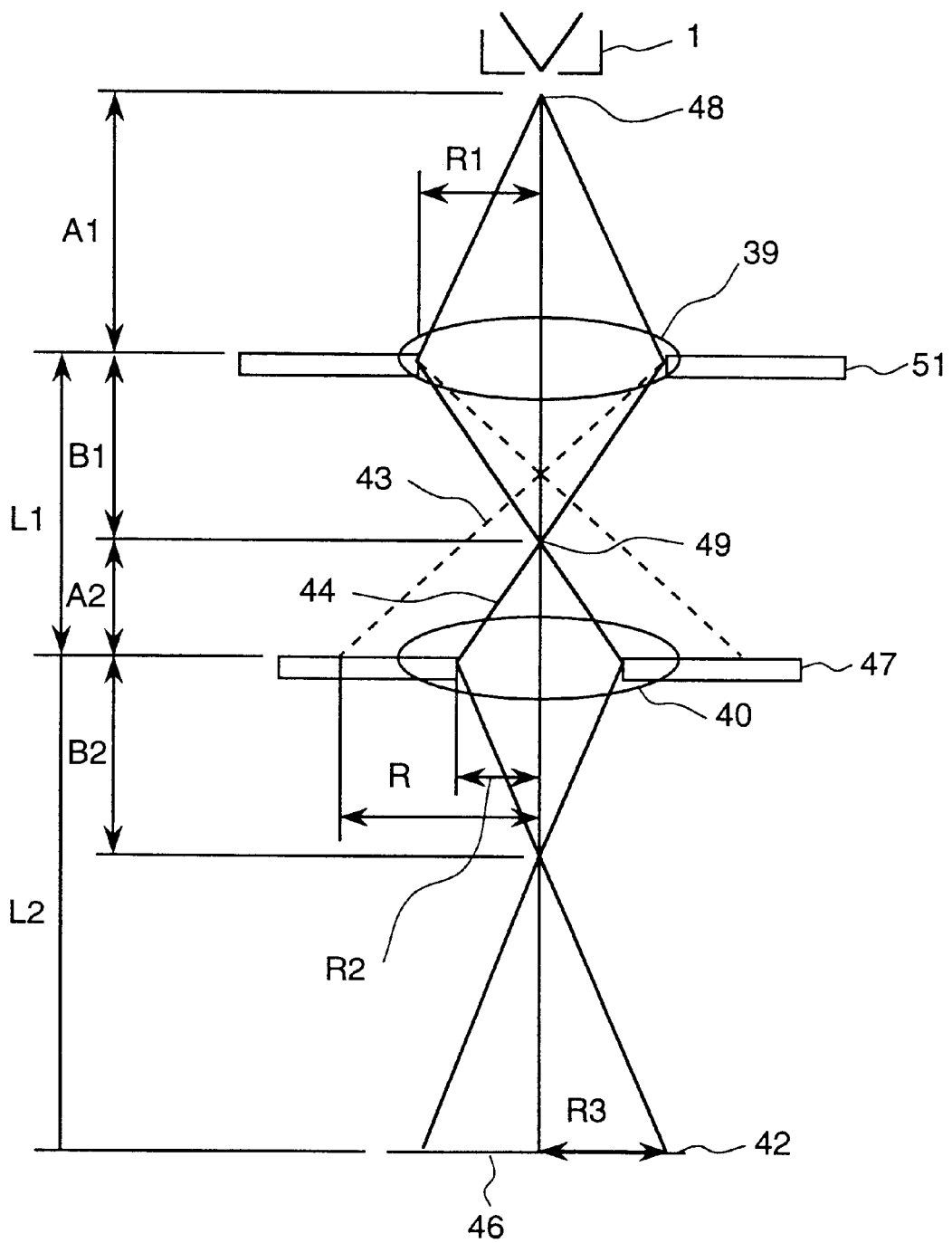
FIG. 10 is a ray diagram of an example of an irradiation lens system.

From FIG. 10, the following equation 15 and 16 are satisfied.

$$A_2 = L_1 - f \quad (15)$$

$$\frac{R_2}{B_2} = \frac{R_3}{L_2 - B_2} \quad (16)$$

The value $B_2$ can be expressed by the following equation 17.

$$B_2 = L_2 \frac{R_2}{R_2 + R_3} \quad (17)$$

From the equation 7 described above, the focal length f' and the lens current value i' of the second irradiation lens 40 becomes the following equation 18 where D is a constant.

$$f' = \frac{D}{i'^2} \quad (18)$$

By substituting the equations 15, 17 and 18 into the equation 14, the following equation 19 can be obtained.

$$i'^2 = D \frac{L_2 \times R_2 + (L_1 - f)(R_2 + R_3)}{(L_1 - f) \times R_2 \times L_1} \quad (19)$$

By substituting the equation 7 described above into the equation 19, the following equation 20 can be obtained.

$$i'^2 = D \frac{\left(L_1 - \frac{C}{i^2}\right)(R_2 + R_3) + L_2 \times R_2}{\left(L_1 - \frac{C}{i^2}\right) \times R_2 \times L_2} \quad (20)$$

The second irradiation lens current i' can be calculated by inputting the first irradiation lens current i and the radius $R_3$ of the electron beam irradiation region into the equation 20.

As described above, by inputting an irradiation electron beam density j on the sample surface and the radius $R_3$ of the electron beam irradiation region into the relational equations, the first irradiation lens current i and the second irradiation lens current i' for obtaining the irradiation electron beam density j and the electron beam irradiation region (radius $R_3$) can be calculated using the equation 13 and the equation 20.

Figure 2:
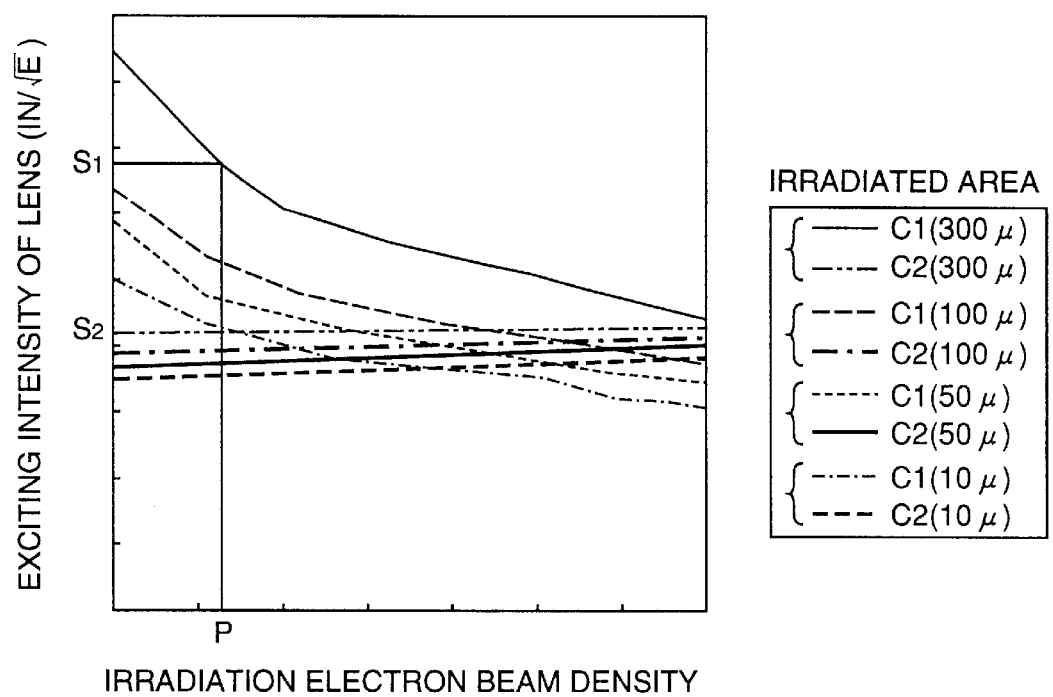
FIG. 2 is a graph showing electron optical characteristics of an irradiation lens system of a transmission electron microscope.

Otherwise, the condition of the first irradiation lens current i and the second irradiation lens current i' for obtaining the irradiation electron beam density j and the radius $R_3$ of the electron beam irradiation region may be experimentally obtained. FIG. 2 is a graph showing the electron optical characteristics of an irradiation lens system of a transmission electron microscope. The graph shows an example of the relationship among the irradiation electron beam density and the exciting intensity of the first irradiation lens and the exciting intensity of the second irradiation lens, and the relationship is experimentally obtained with parameters of the irradiation regions of the irradiation electron beam having radiuses 300 μm, 100 μm, 50 μm and 10 μm. The abscissa is the irradiation electron beam density. The ordinate is the exciting intensity which is expressed by $I \cdot N \cdot E^{-\frac{1}{2}}$ where I is lens current, N is number of turns of the coil, and E is acceleration voltage corrected by the theory of relativity. In the graph, the curve C1 and the curve C2 are shown in a pair for each of the irradiation regions having the radiuses 300 μm, 100 μm, 50 μm and 10 μm. The curve indicated by C1 corresponds to the first irradiation lens and the curve indicated by C2 corresponds to the second irradiation lens.

For example, in the electron beam irradiation region having a radius of 300 μm shown in FIG. 2, a first irradiation lens current and a second irradiation lens current for satisfying an irradiation electron beam density P are obtained in a manner as follows. As shown in the figure, an exciting intensity $S_1$ of the first irradiation lens and an exciting intensity $S_2$ of the second irradiation lens at the irradiation electron beam density P are obtained from the pair of curves C1 and C2 for the irradiation region 300 μm. As the values of the exciting intensities of the lenses are known, a lens current $I_1$ of the first irradiation lens and a lens current $I_2$ of the second irradiation lens can be calculated from the following equation 21 since the values of the exciting intensities of the lenses are expressed by the relation of $I \cdot N \cdot E^{-\frac{1}{2}}$. Therein, $N_1$ is number of turns of the coil of the first irradiation lens, and $N_2$ is number of turns of the coil of the second irradiation lens.

$$I_1 = S_1 \times \frac{\sqrt{E}}{N_1}$$
$$I_2 = S_2 \times \frac{\sqrt{E}}{N_2}$$
(21)

When each of the lens currents of the irradiation lens system is determined from the calculation or the experimental data as described above, each of the lens current is written in a control unit of digital-analog converter (hereinafter referred to as DAC) of each lens as data. The content of the control unit of DAC is output as a lens current for each lens through a power source for the each lens current.

In the present invention, a control unit reads sample positional information at that time, and displays the electron beam irradiated region by placing the present sample position at the center on a display unit such as a CRT in a form of a graphic. When the sample position is changed using a sample fine movement apparatus while the sample is under an electron beam irradiation state, the display of the region irradiated with the electron beam is moved as the sample position is changed. Therein, if the region before the movement is displayed together with the changed position, the region which has been irradiated is also displayed. Further, if an electron beam irradiation region and an irradiation electron beam density are known by measuring a sample position and an irradiation period at the position, distribution of the quantity of irradiation electron beam within a region which has been irradiated on the sample surface can be calculated. Therefore, by displaying the region by changing brightness (halftone) or display color corresponding to the quantity of the irradiation electron beam, the distribution of the quantity of irradiation electron beam within the region which has been irradiated can be understood at a glance.

Referring to ray diagrams of the irradiation lens system shown in FIG. 3 to FIG. 6, description will be made below on operations of the first irradiation lens and the second irradiation lens for changing irradiation electron beam density while an electron beam irradiation region is being kept constant. FIG. 3 to FIG. 6 show electron optical conditions different in position and number of forming crossover of the electron beam. However, in any of the conditions, the irradiation electron beam density can be changed while an electron beam irradiation region is being kept constant. Therefore, the description will be made, referring to FIG. 3.

Figure 3:
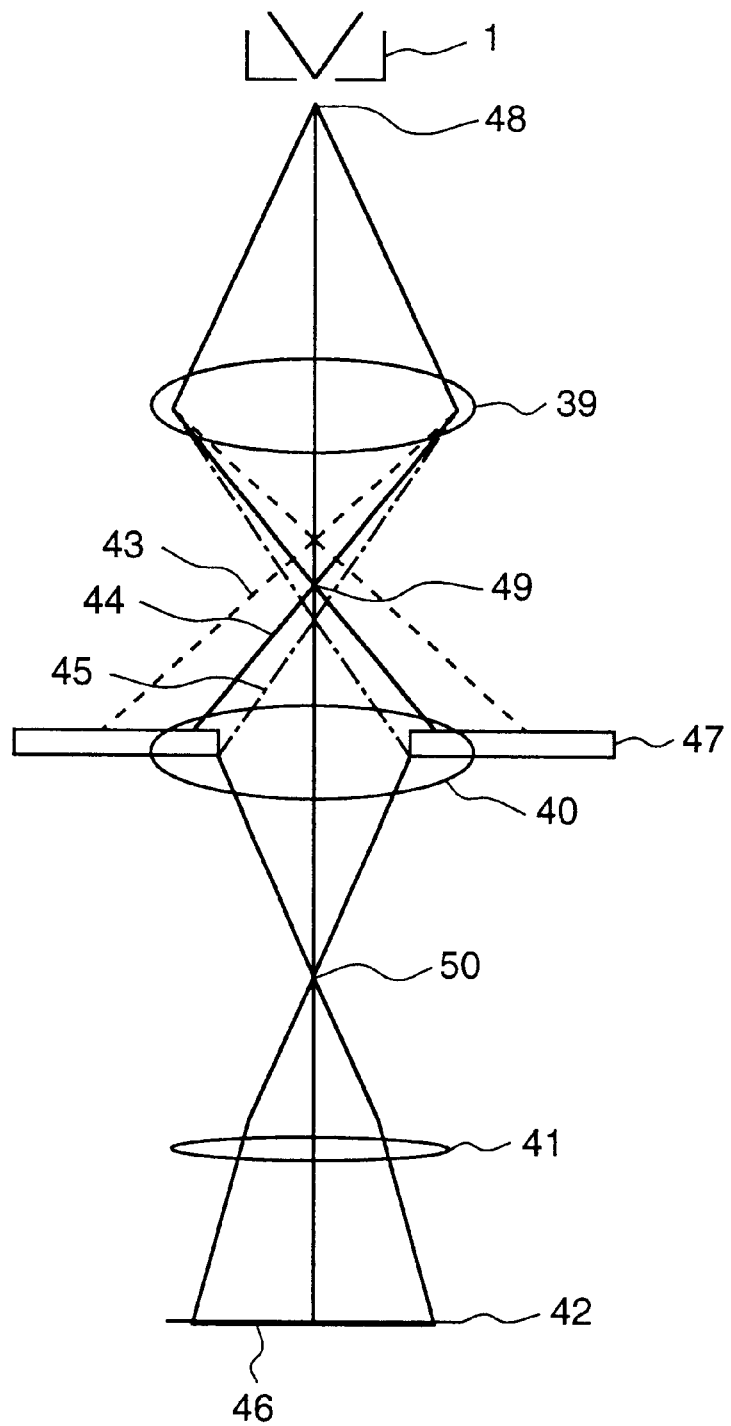
FIG. 3 is a ray diagram of an irradiation lens system.
Figure 4:
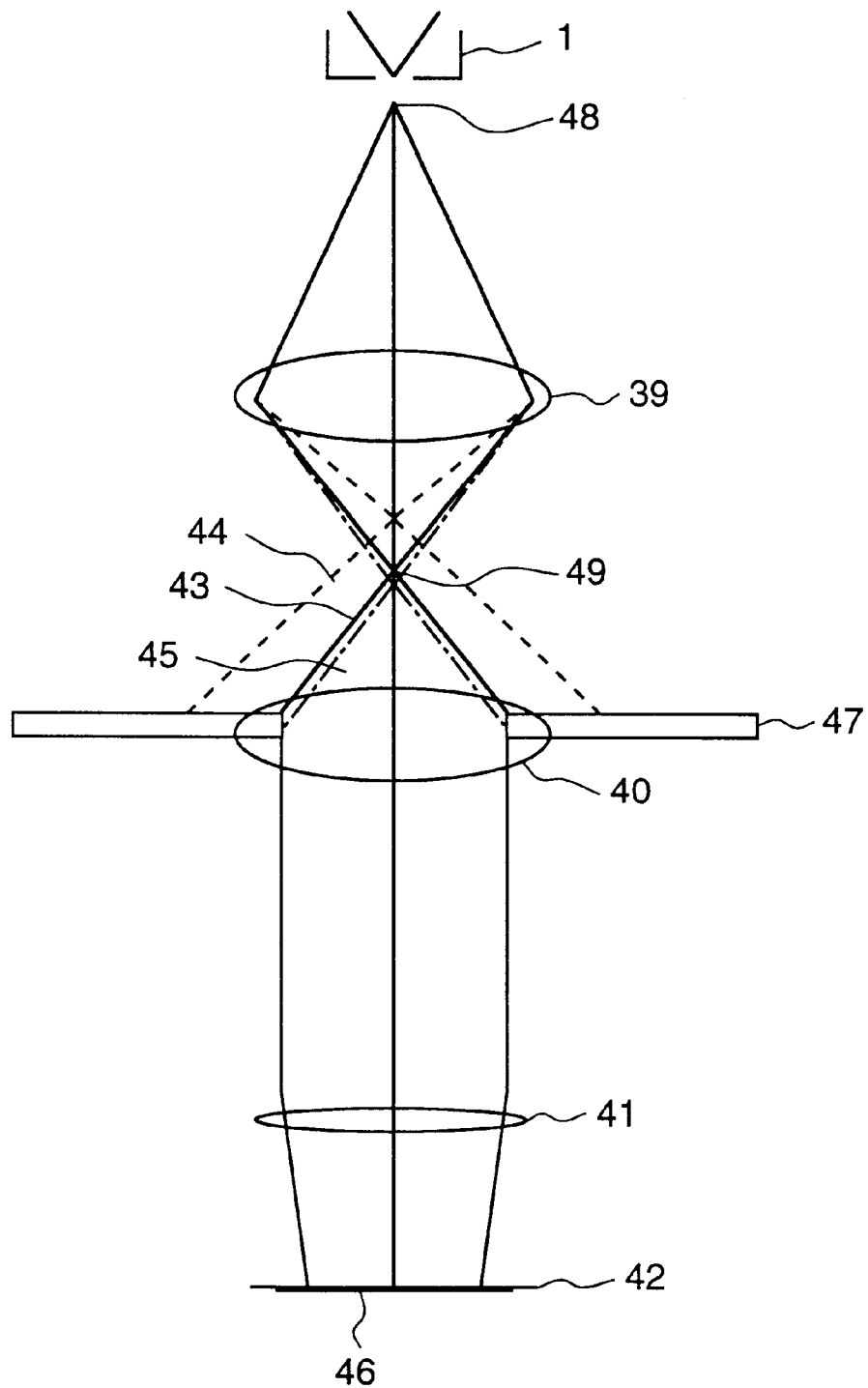
FIG. 4 is a ray diagram of an irradiation lens system.
Figure 5:
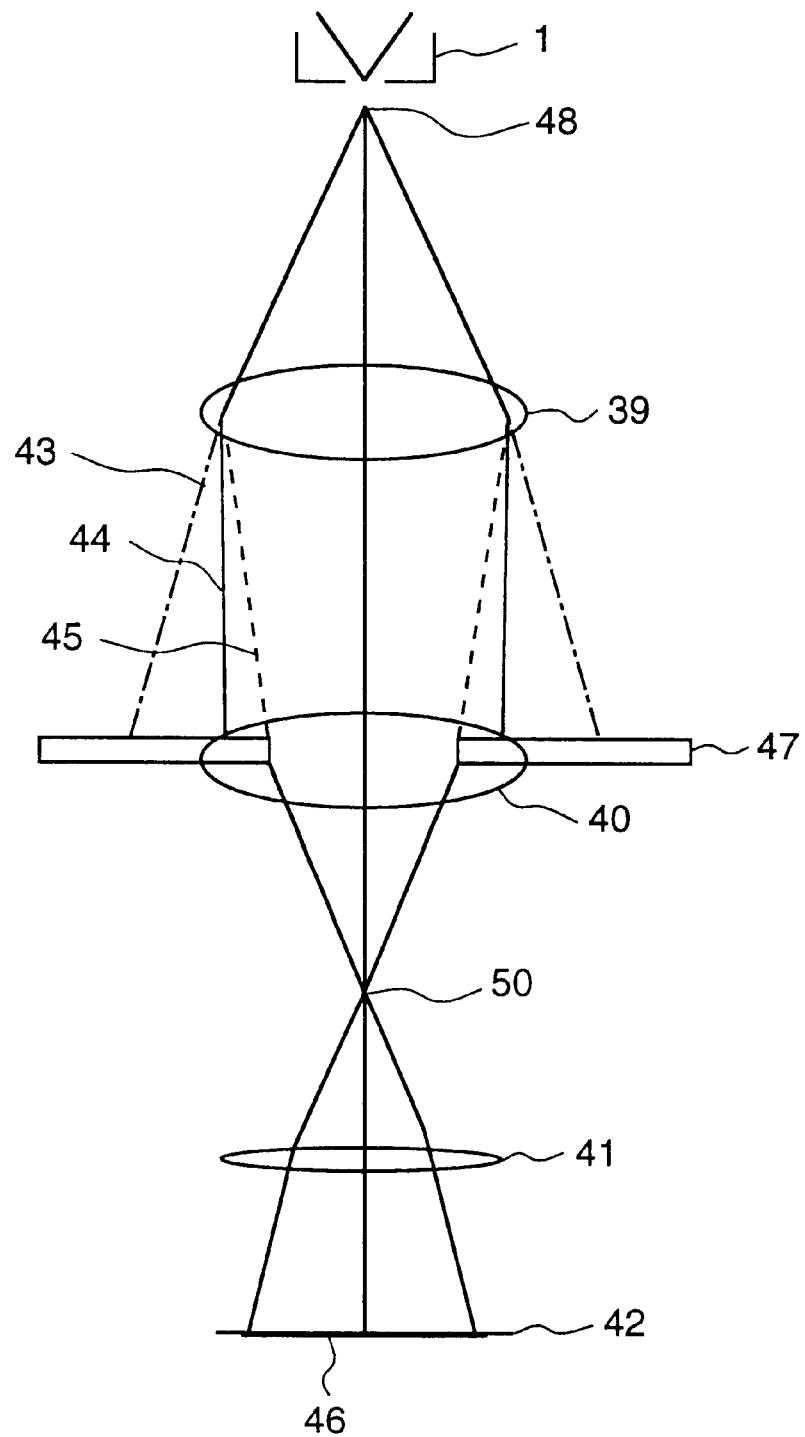
FIG. 5 is a ray diagram of an irradiation lens system.
Figure 6:
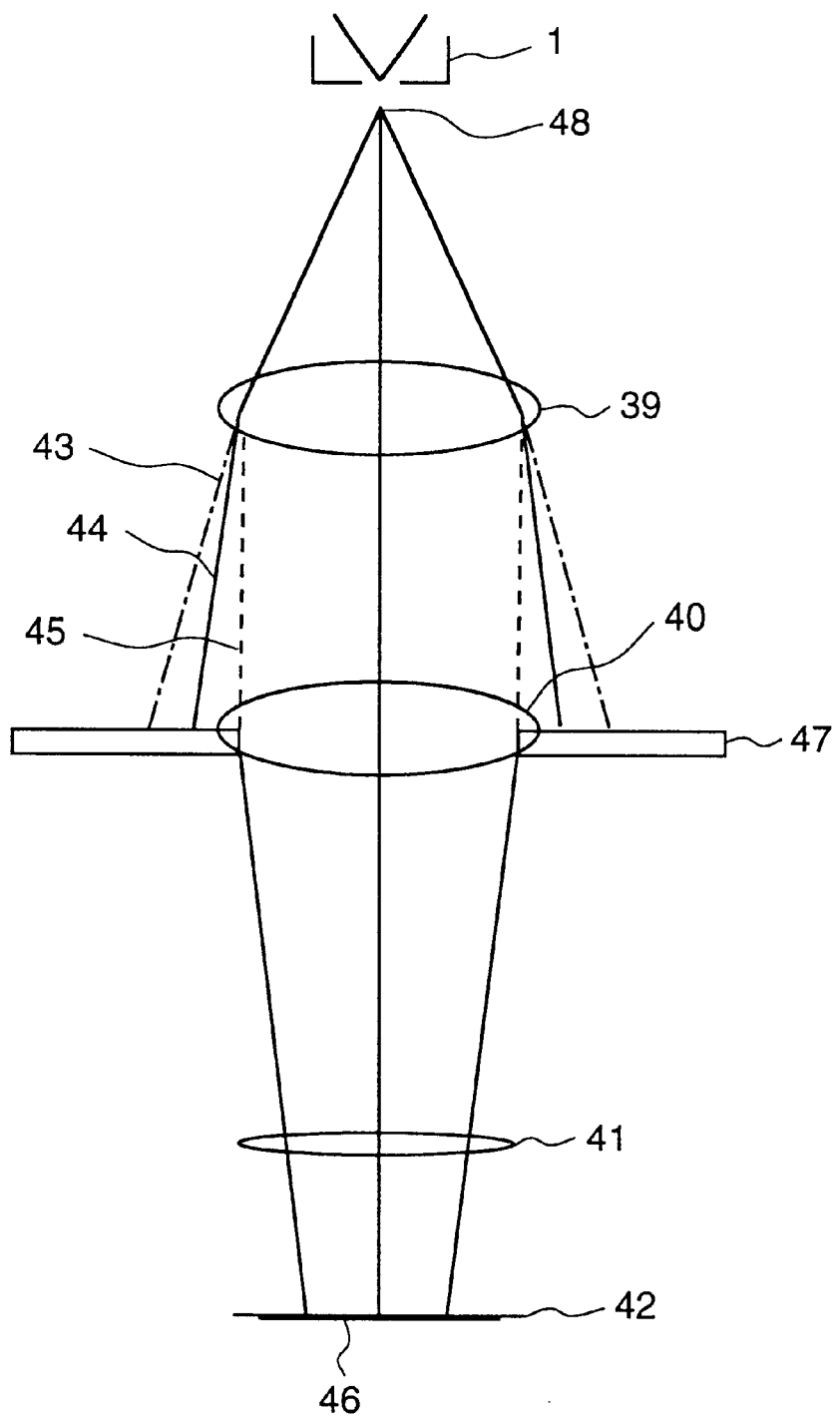
FIG. 6 is a ray diagram of an irradiation lens system.

In the electron optical condition of FIG. 3, a crossover 48 is generated in the electron gun 1, and a crossover 49 is formed by the first irradiation lens 39. A crossover 50 is formed by the second irradiation lens 40 and then a sample 42 is irradiated with the electron beam. An irradiation region 46 on the sample surface with the electron beam is determined by a lens 41 disposed between the crossover 50 and the sample 42. Therein, when the first irradiation lens 39 is strongly excited, the demagnification of the lens is increased. As the first irradiation lens 39 is excited stronger, the quantity of the electron beam cut by the irradiation lens aperture 47 is increased more as shown by a dash-dot line 45, a solid line 44 and a dashed line 43.

Since the quantity of irradiation electron beam of the electron beam passing through the hole of the irradiation lens aperture 47 is reduced by the quantity of the electron beam cut by the aperture, the irradiation electron beam density of the electron beam passing through the hole of the irradiation lens aperture 47 can be reduced by adjusting the exciting intensity of the second irradiation lens 40 so that the electron beam irradiation region 46 becomes the same area as before. As described above, the irradiation electron beam density can be changed without changing the electron beam irradiation region by the combination of the first and the second irradiation lenses.

The electron optical conditions of FIG. 3 to FIG. 6 will be briefly described below. The electron optical condition of FIG. 3 has the crossovers 49 and 50 in the upper side and the lower side of the irradiation lens aperture 47 respectively, and is easy to be used when an area of the irradiation region is small. The electron optical condition of FIG. 4 has one crossover 49 in the upper side of the irradiation lens aperture 47, and is convenient when a wide view field is irradiated. The electron optical condition of FIG. 5 has one crossover 50 in the lower side of the irradiation lens aperture 47, and is easy to be used when an area of the irradiation region is large. The electron optical condition of FIG. 6 does not have any crossover in the upper side and the lower side of the irradiation lens aperture 47, and is convenient when a wide view field is irradiated. In any of the electron optical conditions, the irradiation electron beam density is adjusted by changing the exciting intensity of the first irradiation lens 39, and the electron beam irradiation region is adjusted by changing the exciting intensity of the second irradiation lens 40.

According to the present invention, only a region on a sample surface necessary for observing an image or taking a picture of the image can be irradiated with the electron beam. In other words, since unnecessary irradiation on the sample with the electron beam is not performed, damage of the sample by the electron beam irradiation can be reduced. For example, since the area of the electron beam irradiation region of the sample can be changed while the irradiation electron beam density is being kept constant, the view region capable of being observed can be changed without changing a brightness of an enlarged image. Accordingly, the high magnification image can be observed with a wide view field at once, which improves the capability of observation.

Further, since a quantity of the irradiation electron beam in the electron beam irradiated region of the sample can be easily recognized visually, it is possible to easily select a view field to be observed or to be formed into a picture. Thereby, the efficiency of microscopic examination can be substantially improved.

FIG. 1 is a schematic diagram showing the construction of a transmission electron microscope in accordance with the present invention. Since number of lens stages in the irradiation lens system does not affect the essential operation, description will be made here on a general case of two stages as an example.

An electron beam emitted from an electron gun 1 is directed to a sample through a first irradiation lens formed by a first irradiation lens coil 2 and a second irradiation lens formed by a second irradiation lens coil 3 and an objective lens formed by an objective lens coil 4 to thereby irradiate the sample with the electron beam. The electron beam transmitted through the sample is focused to form an image on a fluorescent plate or the like through a first intermediate lens formed by a first intermediate lens coil 5, a second intermediate lens formed by a second intermediate lens coil 6, a first projection lens formed by a first projection lens coil 7 and a second projection lens formed by a second projection lens coil 8. The sample image is picked up by a TV camera 34. The TV camera 34 is controlled by a TV camera control unit 33, and the sample image picked up is stored in an image memory unit 32. The positional control of the sample is performed by controlling a sample fine movement mechanism 31 using a sample fine movement controller 30.

Each of the lens coils 2 to 8 is excited by each of exciting power sources 9 to 15, and an exciting intensity of each of the lenses is determined by a set value of each of DACs 16 to 22 connected to each of the power sources. Control of the whole system is performed by a microprocessor 23 connected to the DACs 16 to 22, the sample fine movement controller 30 and the image memory unit 32 through a bus. A memory unit 24 for storing operating conditions of the apparatus and various kinds of data, an arithmetical and logical unit 25, a clock 26, a CRT controller 27 for controlling a CRT 35 as a display unit, a keyboard 38 as an input means and interfaces (I/F) 28, 29 for input rotary encoders 36, 37 are also connected to the bus.

When a magnification is input, the magnification switching rotary encoder 36 is rotated to generate a pulse wave, and the generated pulse wave is input to the I/F 28 to convert to a digital signal. The microprocessor 23 converts the digital signal to a numerical value of the magnification by referring a magnification display table preset in the memory unit 24, and displays the corresponding numerical value of the magnification on the CRT 35 using the CRT controller 27. At the same time, the microprocessor 23 outputs magnification data for the objective lens, the first intermediate lens, the second intermediate lens, the first projection lens and the second projection lens (hereinafter referred to as image forming lens system) pre-stored in the memory unit 24 to the DACs 18 to 22 to convert the data for the image forming lens system to analog signals. The analog signals are respectively output from the DACs 18 to 22 to the exciting power sources 11 to 15 to respectively output currents to the lens coils 4 to 8 of the image forming lens system.

A required electron beam irradiation region is selected out of preset electron beam irradiation regions using the keyboard 38. Next, a brightness of the enlarged image, that is, an irradiation electron beam density is input using the input rotary encoder 37. The microprocessor 23 retrieves a combination of current values for the first and the second irradiation lenses out of the memory unit 24 using the input irradiation electron beam density and the input electron beam irradiation region. When any combination of a first irradiation lens current and a second irradiation lens current for the irradiation electron beam density to be set does not exist, a first irradiation lens current and a second irradiation lens current to be set are derived through an interpolation calculation using combinations of data near the irradiation electron beam density using the arithmetic and logical unit 25. Otherwise, using the calculation function, the lens currents are calculated from the relational equations of the irradiation electron beam density and the electron beam irradiation region and the first and the second irradiation lens currents as expressed by the equation 13 and the equation 20 described previously.

After determining each of the lens current values, the lens current values are respectively written in the DACs 16 and 17 for the first and the second irradiation lenses, and the currents are respectively output to the first and the second irradiation lens coils 2 and 3 through the exciting power sources 9 and 10 for the first and the second irradiation lens currents. In a case where the brightness of the enlarged image, that is, the irradiation electron beam density is further changed, an irradiation electron beam density is again input using the input rotary encoder 37, and the irradiation electron beam density is changed by output currents to the first and the second irradiation lens coils 2 and 3 through the means described above.

The TV camera control unit 33 image-displays the enlarged image of the electron microscope projected on the TV camera 34 on the CRT 35. Further, the image can be stored in the image memory unit 32. By calculating the electron beam irradiation region on the sample surface from the data of magnification using the arithmetic and logical unit 25, the magnification is changed by the magnification switching rotary encoder 38. It is possible to set a mode in which currents are output to the first and the second irradiation lens coils by retrieving a combination of the first and the second irradiation lens currents capable of changing only an area of an electron beam irradiation region while the region of the enlarged image projected on the TV camera 34 and the irradiation electron beam density are interlocked with each other at a constant magnification.

Description will be made below on a mode of displaying trails in an irradiation region on the CRT 35 in accordance with the present invention, referring to FIG. 7 to FIG. 9.

Figure 7:
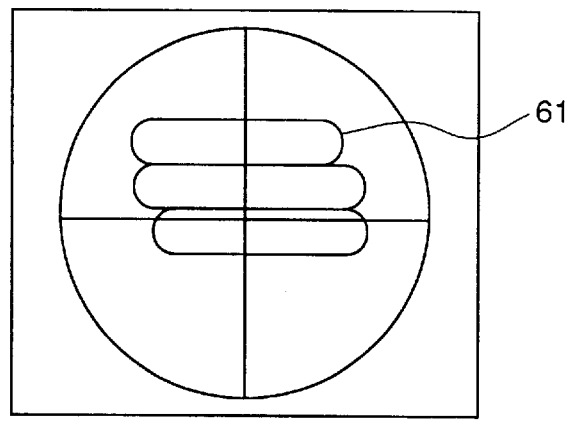
FIG. 7 is a view explaining a mode displaying trails in a region on a sample surface irradiated with an electron beam.

FIG. 7 is a view explaining a mode displaying trails in a region on a sample surface irradiated with an electron beam. In this displaying mode, a region 61 on a sample surface irradiated with an electron beam is displayed based on information on an area of an electron beam irradiation region and sample positional information obtained from the sample fine movement mechanism 31.

Figure 8:
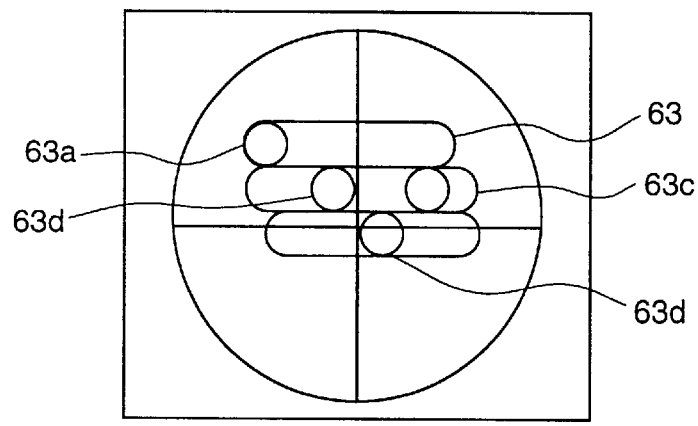
FIG. 8 is a view explaining a mode displaying trails in regions on a sample surface irradiated with an electron beam and a quantity of irradiation electron beam in each region.

FIG. 8 is a view explaining a mode displaying trails in regions on a sample surface irradiated with an electron beam and a quantity of irradiation electron beam in each region. In this displaying mode, a region 63 on a sample surface irradiated with an electron beam is displayed with changing corresponding to a quantity of the irradiation electron beam based on an area of the electron beam irradiation region, an irradiation electron beam density, an irradiation time period and sample positional information obtained from the sample fine movement mechanism. The quantity of the irradiation electron beam is displayed by changing brightness (halftones) or display color corresponding to a quantity of irradiated electron beam. For example, in the CRT display of FIG. 8, it can be understood at a glance that the regions 63*a* to 63*d* more than the other regions is irradiated with the electron beam.

Figure 9:
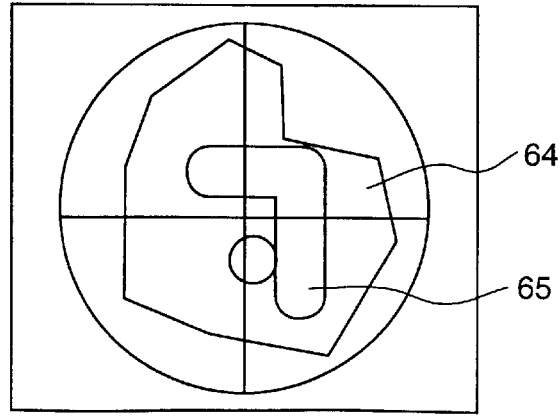
FIG. 9 is a view explaining a mode displaying the trails in regions on a sample surface irradiated with an electron beam overlapping onto the sample image.

FIG. 9 is a view explaining a mode displaying the trails in regions on a sample surface irradiated with an electron beam overlapping onto the sample image. In this mode, the region 65 irradiated with the electron beam is displayed by overlapping on an enlarged image 64 of a sample. The image of the whole sample is acquired in advance by the TV camera 34 using the TV camera control unit 33, and the enlarged image is stored in the image memory unit 32. Then, the image data is output to the CRT controller 27 to display the whole image 64 of the sample on the CRT 35. After that, pulse waves output from the sample fine movement mechanism 31 is input to the sample fine movement control unit 30 to convert to sample positional data. The region irradiating the present time is displayed from the data of the magnification, the sample position and the electron beam irradiation region using the arithmetic and logical unit 25 in a form of graphic by color information overlapping on the image of the whole sample. Next, a time period during which the sample is irradiated is measured using the time measuring unit 26. A quantity of irradiation electron beam is calculated from the time period during which the sample is irradiated and the irradiation electron beam density using the arithmetic and logical unit 25, and the trails in regions on the sample surface irradiated with the electron beam is changed in brightness (halftone) or color corresponding to the calculated quantity of irradiation electron beam and then displayed and overlapped on the image of the whole sample. Therein, it is preferable that the displaying color of the irradiated region is different from the color of the sample image so that the sample image is not masked by the display of the electron beam irradiation region.

The microprocessor 23 acquires data of a sample position from the sample fine movement control unit 30 every time when the sample position is set. When the sample position is changed, a trail 65 of the electron beam irradiation region on the sample surface is displayed on the CRT image by changing the display position of the electron beam irradiation region from the changed sample position. Further, the trails of the electron beam irradiation region on the sample surface is displayed and overlapped on the CRT image by changing brightness (halftone) or color corresponding to the quantity of irradiation electron beam.

Description will be made below on a method of changing an irradiation electron beam density or an area of the electron beam irradiation region together with a magnification.

Initially, description will be made on a case where only the area of the electron beam irradiation region is changed while the irradiation electron beam density is not changed. The microprocessor 23 receives information of an irradiation electron beam density from the inputting rotary encoder 37, and retrieves a combination of current values for the first and the second irradiation lenses, which makes the irradiation electron beam density constant, out of the memory unit 24 using the input irradiation electron beam density and the input electron beam irradiation region. When any combination of a first irradiation lens current and a second irradiation lens current for the irradiation electron beam density to be set does not exist, a first irradiation lens current and a second irradiation lens current to be set are derived through an interpolation calculation using combinations of data near the irradiation electron beam density using the arithmetic and logical unit 25. The first irradiation lens current and the second irradiation lens current are set to the DACs 16 and 17, and the exciting power sources 9 and 10 output the set first irradiation lens current and the set second irradiation lens current to the first and the second irradiation lenses, respectively. The microprocessor 23 displays the electron beam region after changed on the CRT 35 in a form of graphic using data on the changed electron beam irradiation region and the sample position.

In a case of performing the control in which the electron beam irradiation region is switched while the irradiation electron beam density is being kept constant for each magnification, an area of the electron beam irradiation region corresponding the magnification is calculated using the arithmetic and logical unit 25, and the microprocessor 23 retrieves a combination of current values for the first and the second irradiation lenses out of the data stored in the memory unit 24 which makes the irradiation electron beam density constant. After determining each of the lens current values, the lens current values are respectively written in the DACs 16 and 17 for the first and the second irradiation lenses, and the currents are respectively output to the first and the second irradiation lens coils 2 and 3 through the exciting power sources 9 and 10 as the first and the second irradiation lens currents. The image of the electron beam irradiation region at that time is displayed on the CRT 35.

In a case of performing the control in which the irradiation electron beam density is switched so that a current value on the fluorescent plate becomes constant while the area of the electron beam irradiation region is being kept constant for each magnification, an irradiation electron beam density corresponding the magnification is calculated using the arithmetic and logical unit 25, and the microprocessor 23 retrieves a combination of current values for the first and the second irradiation lenses out of the data stored in the memory unit 24 which makes the area of the electron beam irradiation region constant. After determining each of the lens current values, the lens current values are respectively written in the DACs 16 and 17 for the first and the second irradiation lenses, and the currents are respectively output to the first and the second irradiation lens coils 2 and 3 through the exciting power sources 9 and 10 as the first and the second irradiation lens currents. The image of the electron beam irradiation region at that time is displayed on the CRT 35.

Similarly, it is also possible to control the area of the electron beam irradiation region and the irradiation electron beam density so that the brightness of an observed image becomes constant for each magnification. In this case, an irradiation electron beam density corresponding to the magnification is calculated by the arithmetic and logical unit 25 and at the same time an area of the electron beam irradiation region corresponding to the magnification is calculated by the arithmetic and logical unit 25 so that the current value on the fluorescent plate becomes constant, and then a combination of a first and a second irradiation lens currents satisfying the both conditions is retrieved out of the data stored in the memory unit 24. After determining each of the lens current values, the lens current values are respectively written in the DACs 16 and 17 for the first and the second irradiation lenses, and the currents are respectively output to the first and the second irradiation lens coils 2 and 3 through the exciting power sources 9 and 10 as the first and the second irradiation lens currents. The image of the electron beam irradiation region at that time is displayed on the CRT 35.

As having been described above, according to the present invention, damage of a sample by an electron microscope can be reduced. Further, the efficiency of selecting a view field can be improved, and accordingly the observation capability and the operability of the electron microscope can be improved.

What is claimed is:

1. An electron microscope comprising irradiation lenses and a sample fine movement apparatus, and a sample surface being irradiated with an electron beam focused by the lenses, which further comprises:

means for causing said electron microscope to irradiate each of a plurality of coordinates of the sample surface with a quantity of radiation from the electron beam based on information on the region irradiated with the electron beam and sample position information for that coordinate from the sample fine movement apparatus; and means for displaying a locus of regions on the sample surface irradiated with the electron beam based on said information on the region irradiated with the electron beam and sample position information from the sample fine movement apparatus, the irradiated regions being displayed so as to be distinguishable from other regions on the sample surface.

2. An electron microscope according to claim 1, which further comprises means for picking up a enlarged image of the electron microscope; and means for displaying the picture of the image picked up, said display of the region of the sample surface irradiated with the electron beam being displayed by overlapping onto the enlarged sample image picked up.

3. An electron microscope according to claim 1, wherein said locus of regions is displayed in superposition on a low magnification electron microscope image.

4. An electron microscope comprising irradiation lenses and a sample fine movement apparatus, a sample being irradiated with an electron beam focused by the electron lenses, which further comprises:

means for causing said electron microscope to irradiate each of a plurality of coordinates of the sample surface with a quantity of radiation from the electron beam based on information on the region irradiated with the electron beam and sample information for that coordinate from the sample fine movement apparatus; and means for displaying regions on the sample irradiated with the electron beam on said basis of the region on the sample irradiated with said electron beam, an irradiation electron beam density, an irradiation time period and sample position information from the sample fine movement apparatus, the displayed regions being varied in brightness or color depending on said quantity of the irradiated electron beam.

* * * * *